United States Patent
Zhang

(10) Patent No.: US 9,402,378 B2
(45) Date of Patent: Aug. 2, 2016

(54) MINI SPACE FARM-A FOOD REGENERATIVE SYSTEM IN THE LONG-TERM SPACE MISSION

(76) Inventor: Mao Zhang, Fontana, CA (US)

( * ) Notice: Subject to any disclaimer, the term of this patent is extended or adjusted under 35 U.S.C. 154(b) by 511 days.

(21) Appl. No.: 13/201,621

(22) PCT Filed: Oct. 25, 2009

(86) PCT No.: PCT/US2009/061985
§ 371 (c)(1), (2), (4) Date: Aug. 15, 2011

(87) PCT Pub. No.: WO2010/096107
PCT Pub. Date: Aug. 26, 2010

(65) Prior Publication Data
US 2011/0296756 A1     Dec. 8, 2011

(30) Foreign Application Priority Data
Feb. 23, 2009    (CN) .......................... 2009 1 0046463

(51) Int. Cl.
| | | |
|---|---|---|
| A01K 29/00 | (2006.01) | |
| A01K 67/033 | (2006.01) | |
| A01K 5/00 | (2006.01) | |
| A01K 39/00 | (2006.01) | |

(52) U.S. Cl.
CPC ................. *A01K 67/033* (2013.01); *A01K 5/00* (2013.01); *A01K 29/00* (2013.01); *A01K 39/00* (2013.01); *A01K 67/0332* (2013.01)

(58) Field of Classification Search
CPC .. A01K 29/00; A01K 67/033; A01K 67/0332
USPC .............................. 47/59 R; 119/6.5, 6.6, 6.7
See application file for complete search history.

(56) References Cited

U.S. PATENT DOCUMENTS

| | | | |
|---|---|---|---|
| 6,938,574 | B2 | 9/2005 | Zhang |
| 2003/0233982 | A1 | 12/2003 | Zhang |

FOREIGN PATENT DOCUMENTS

| | | |
|---|---|---|
| CN | ZL03115847.1 | 9/2008 |
| CN | 200910046463.0 | 8/2010 |

*Primary Examiner* — Monica Williams

(57) ABSTRACT

In the long-term space human living environment, the biological wastes from human, animals, and plants can be fully digested and recycled by rearing six kinds of recycling animals which will be nourishing feed stuff for feeding edible animals. These edible animals and their eggs combined with space plants will be various food for human. Water and nutrition left in the residues after rearing these feedstuff recycling animals can be recycled and used to fertilize plants. All the animals and plants can be solidly reared in same cabin on the shelf with high densities in boxes, cages, trays and tanks which are all in minimum volume and weight. It is the basis for realizing mini space farm which provides a self-sufficient food regenerative system that enable humans to live and work in space independent of food supply from earth.

5 Claims, 2 Drawing Sheets

MINI SPACE FARM-A FOOD REGENERATIVE SYSTEM IN THE LONG-TERM SPACE MISSION

This application is the national stage of PCT/US2009/061985, filed on Oct. 25, 2009

BACKGROUND OF THE INVENTION (1) Field of the Invention

A self-sufficiency food production method in the closed human living environment of long-term space missions. In particular by rearing of a variety of animals and plants, to realize efficient recycling of all the biological wastes to food sources with minimum weight and volume.

(2) Background Art

To date, all crewed space missions have been short-term and in low earth orbit. They have to rely on food replenishment from earth. Wastes must be discarded or stored until the crew return to earth. But for future long-term missions and permanent planetary bases such as those on the moon and Mars, it will not be possible to supply the space human from earth. The recovery and recycling of nutrients from wastes to support food production must be performed in the space. However, current technology cannot support this goal. For example, NASA's crop-plant-based bioregenerative systems satisfy only a fraction of the total waste recycling (mainly $CO_2$ and gray water) and food requirements. These systems also require high levels of light energy for maximum photosynthesis, large growing areas, and long growing periods. So current NASA Advanced Life Support technology cannot provide the life support functions needed for long term human space exploration in a cost-effective manner. It is beneficial to recycle the solid wastes, particularly if bioregenerative systems are used to process waste materials for producing food. Some researchers in NASA and relevant institutions has developed the technologies to recycle nutrients from human dejection, but so far no one can know how to convert human dejection to nourishing food directly.

As to applicant's previous US patent (U.S. Pat. No. 6,938,574), it is to rear fly maggots in space for digesting and recycling the feces from human and terraneous animals, and a part of the bio-wastes from animals and plants, it is an effective way to convert human dejections to nourishing food resource directly. But maggots can not recycle most of the bio-wastes from plants and animals, such as all stems, leafves, shells, roots, peelings of space plants; and feathers, squamae, bones, the other residues of space animals; as well as the feces from aquatic animals. Not even to mention to recycle great amount of the organic plastic in the space. These wastes has to be recycled to support food regeneration in the space by an effective way to be found.

BRIEF SUMMARY OF THE INVENTION

In this invention we propose rearing six types of small animals which are mainly insects, all the biological wastes (bio-wastes) in the space human life environment, including the human and animal feces, inedible parts of the plants and animals, food bits and other bio-wastes, plus the organic plastics, can be feedstuff for rearing these six small animals, they can recycle and digest all the wastes to be their nourishing biomass. The biomass of these six animals, combine with the inedible parts of the space plants, will further be used as feedstuff for feeding edible animals of poultry, aquatics, amphibians, livestock. The meat, eggs and milk from these edible animals are taken as human's animal food. Here we name these animals are as Edible Animals (EA), these six small animals are as Recycling Animals (RA).

The water and nutrition left in the residues after rearing the RA can be recycled and used to fertilize the space plants. The space plants can also be cultivated as vegetarian food which have successfully developed by NASA and other countries.

These RA have strong reproduction abilities, short life cycle, and can be easily reared in high densities with high efficiency in microgravity. The rearing boxes for these RA are all in minimum volume and weight which is the basis for realizing mini space farm.

Rearing RA, EA in combination with growing space plants can provides a self-sufficient food regenerative system with minimum volume, weight, energy, labor and cost in the long term space missions.

DETAILED DESCRIPTION OF THE INVENTION

Figure 1:
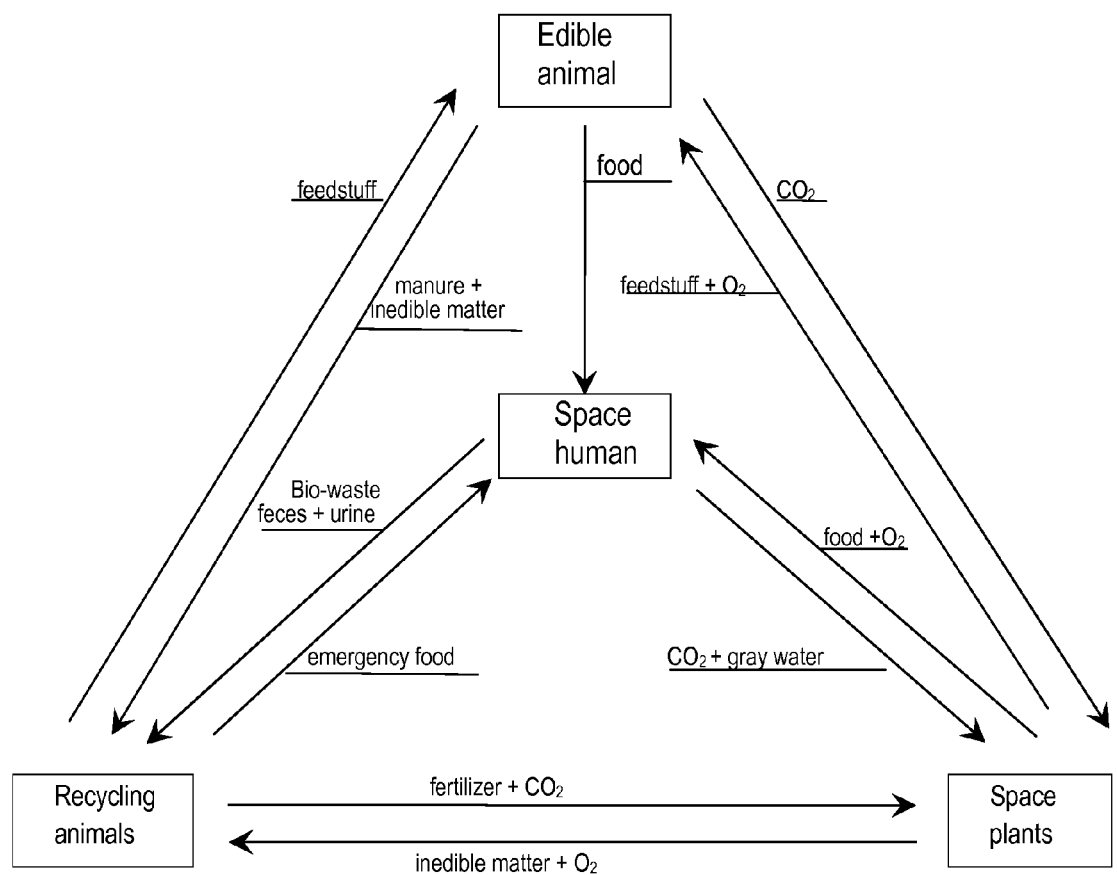
FIG. 1: A closed bio-regenerative life support system by cultivating of the animals and plants to recycle all the bio-wastes to be food sources in the long term space human living environment.

The present invention concerns a new closed-loop bio-regenerative life support system, and it can achieve full self-sufficiency in food, and partly in water and air recycling. Here we focus on the function of a food regenerative system. It is a closed ecosystem by recycling all the bio-wastes to be food. This system composes of four parts, namely RA system, EA system, plants system and space human. The animals and plants systems include two types: aquatic and terrestrial. See FIG. 1: this system enables human to realize food regeneration by cultivating of RA, EA and plants in the space. There are four parts of the taches: humans, RA, EA and plants that form a closed-loop food regeneration chain. Each part of the tache has a role in waste recycling and food regeneration:

The RA: recycle all the wastes from other three parts and supply them as animal's feedstuff and human's food; supply $CO_2$ for plant photosynthesis and the residues after rearing RA will be used as fertilizer for plants.

The human: get the food from other three parts and $O_2$ from plant crops, supply the human wastes for rearing RA and supply $CO_2$, gray water for plant crops;

The EA: get the feedstuff from RA and plants, get the $O_2$ from plants, and supply the food for human; provide the wastes for rearing RA, and $CO_2$ for plant crop;

The plants: supply food for human, feedstuff for animals, inedible matter for rearing RA and $O_2$ for other three parts, and get the fertilizer from RA and $CO_2$ from other three parts;

This closed-loop food regeneration system enables human to realize self-sufficiency of the food supply while living in the long-term space missions or living on the permanent planetary bases.

Part One: The Recycling Animals (RA) system:

The RA is the core of this method. we chose these six kinds of insect-based RA for digesting and recycling all the bio-wastes in the space human life environment, to realize efficient production of high-protein, high-nutrient and high-energy biomass with minimal volume and weight. Then the RA as the main feed for rearing the edible animals (EA) which for human consumption in the space, some of RA is also available for direct human consumption. These RA samples were selected as follows:

First, Housefly Larvae (HFL)—Maggot, (*Musca domestica* larvae);
Second, Mealworm (MW), (*Tenebrio molitorLarvae*); Third, Superworm (SW), (*Zophobas morioLarvae*);
Forth, Tubificids (TUB); Fifth, Cladocerans (CLA); Sixth, Earthworm (EW).
Each RA has its own main functions for recycling and digesting wastes:
1) Maggot (HFL) mainly recycle the feces of human and terrestrial animals;
2) MW and SW are able to recycle most bio-wastes that maggot can not eat, including the maggot dung, and the residues, the inedible space plants, such as all the by-products, stems, leaves, roots, shells and skins; and the inedible parts of EA, such as the feathers, bones, scales, skins and organs; and human vomit, food residues, even their bodies selves and all the packaging materials of organic plastic.
3) TUB and CLA can recycle the dung and residues from the aquatic animals, bacterias, algae and other biological residues in the water;
4) EW can recycle all the dung and residues from other RA, and the bio-wastes that other RA never recycle; it also can improve the soil fertility and the structure for the space terrestrial plants. The reasons for selecting these RA are that all of them have the following common characteristics:
1) They have strong vitality, less to fall ill, with a strong environmental suitability;
2) The production technologies are mature, the operation and equipment are simple, so they are easy to feed;
3) The fecundity is strong with a short life cycle and they can reproduce by themselves in the space microgravity environment;
4) Feeding habits are wide and various, all of feeds are bio-wastes. So they will not compete for the food with human being and the edible animals;
5) They are all the scotophilic animals, so when raising, they should be reared in dark boxes instead of in the light as for plant photosynthesis, thus save the energy;
6) They can be continuously fed in 24 hours a day, 365 days a year;
7) Feeding box used to raise terraneous RA, the boxes can be overlapped on the shelf, to realize the solid feeding in the minimum volume;
8) The optimal growth temperature for them is 25-30° C., and the humidity is 65~75%, so they can be fed in the same cabin.
9) TUB and CLA are all aquatic animals, originally live in water, so the space microgravity environment will not influence of their lives. Other four kinds of RA are fed in high density in the conditions of closely contacting with the feeds, and their active space is limited in the feeding box (HFL, MW, SW) or in the soil (EW), so the "space flotation" will not occur under the space microgravity environment, their lives will not be greatly affected;
10) They can reproduce in the space by themselves, however, their eggs and oosperms can be frozen in liquid nitrogen for long-term store and thawing them any time for recovering their ability of reproduction and normal growth in the space, thus to keep the security of the food source.
11) Their nutrient contents are very rich (seeing Table 1) and protein contents in the dry biomass of these RA will reach 50-60%. The crude protein content is very high and the content of essential amine acids for human body contained by them are similar with the fishmeal, and the ingredients are in balance (Table 2). The fat content is rich, the component of fatty acid is in balance, the ratio between the saturated fatty acid and unsaturated fatty acid is below 40%, which is much better than that of beef, mutton, pork, chicken. And their mineral substances, trace elements and vitamin contents are also very rich, the content of cholesterin is low, with few of meat fiber and easy to absorb, it is the better animal protein source than that of the meat and egg. The practice has proved that they are also the best living feeds for almost of the aquatic and terrestrial small animals:

12) They live in piles and in high density condition with very short growth period and high conversion ratio between feed and RA biomass. The biomass yield is very high, which can be seen from Table (3) and that of the first 3 kinds of RA is several hundred or thousand times as high as that of crops in the same area.

The data in Table 1, 2, 3 are from six national academic institutes of China and another from Japanese Rocket Society. (See, Wang Darui et al, Entomological Knowledge 1991 (4): 247-249, "Analysis and utilizing of the Nutritional Contains of Housefly Larvae."; Zhang Zhesheng, et al, Science and Technology of Food Industry 1997 (6): 67-69, "Exploration House Fly Larvae as a Potential Food Protein Resource for Human."; Li Guanghong, et al, Entomological Knowledge, 1997 34 (6): 347-349; "Nutritional evaluation of extracted Housefly Protein."; Wei Yongping et al, China Agriculture Press, Beijing, August 2001, "Raising of Economic Insects and Its Exploitation."; Chen Deniu et al, China Jin Dun Press, Beijing, June 2008; "Raising Technology of Earthworm"; Xu Qiai et al, Anhui Agriculture Science Bull, 2008, 14(21): 158-160; "The Research Progress on Economic Insects of Mealworm and Superworm"; and N. Katayama, et al, J. Space Tech-Science. 2005, 21(2), Journal Society of Japanese Rocket Society. "Entomophagy as Part of a Space Diet for Habitation on Mars"

TABLE 1

Comparison of Nutritional Contents of 3 kinds of RA with fishmeal in the dry powder (%)

| Content | HFL | HF Pupae | MW | MW Pupae | EW | Fishmeal |
|---|---|---|---|---|---|---|
| Protein | 60.88 | 58.2 | 51 | 57 | 56.44 | 60.4 |
| Fat | 17.1 | 14.55 | 34.1 | 36.2 | 7.84 | 8.4 |
| Ash Content | 9.2 | 8.1 | — | — | 8.29 | 17.1 |
| Ca | 0.71 | 0.47 | 1.38 | — | 0.94 | 3.43 |
| P | 2.52 | 1.71 | 6.83 | — | 0.10 | 3.08 |

TABLE 2

Comparison of Essential Amino Acids (EAA) content of 3 kinds of RA with fishmeal in the dry powder (%)

| | Mensurated Item | | | | | |
|---|---|---|---|---|---|---|
| EAA | HFL | HF Pupae | MW | MW Pupae | EW | Fishmeal | FAO |
| Threonine | 2.34 | 2.19 | 1.33 | 2.08 | 2.87 | 3.17 | 4.2 |
| Leucine | 3.57 | 3.45 | 2.48 | 3.25 | — | 5.17 | 4.8 |
| Lysine | 4.30 | 3.80 | 2.47 | 2.22 | 4.57 | 5.42 | 4.2 |
| Phenylalanine | 4.32 | 3.42 | 0.78 | 0.74 | 2.58 | 2.66 | 2.8 |
| Tyrosine | 4.30 | 3.24 | 2.64 | 2.48 | — | 1.98 | 2.8 |
| Methionine | 1.49 | 2.47 | 0.36 | 0.74 | 1.25 | 1.53 | 2.2 |
| Threonine | 2.30 | 2.24 | 1.77 | 1.78 | 3.32 | 2.59 | 2.8 |
| Tryptophan | 0.78 | 0.69 | 0.36 | 0.36 | 0.84 | 0.76 | 1.4 |
| Cystine | 0.43 | 0.64 | 0.35 | 0.19 | 0.91 | 0.56 | — |
| Valine | 2.76 | 2.61 | 3.29 | 3.22 | 2.98 | 3.34 | 4.2 |

Note:
FAO indicates the amino acid standard from the Food and Agriculture Organization of the United Nations

TABLE 3

Comparison of yield and nutrition of 3 kinds of living RA with Space crops

|  | Yield g/m² | Grow term Days | Daily Yield (DY) g/m²·d | DY rate with wheat | Protein content g/100 g |
|---|---|---|---|---|---|
| HFL | 4000 × N* | 4 | 1000 × N | 752N | 60.88 |
| MW | 5000 × N | 90 | 55.6 × N | 41.8N | 51 |
| SW | 5000 × 5**N | 90 | 278 × N | 209N | 51 |
| Rice | 526 | 120 | 4.38 | 3.3 | 6.8 |
| Wheat | 280 | 210 | 1.33 | 1 | 10.6 |
| Bean | 367 | 105 | 3.49 | 2.6 | 35.3 |
| Sweet Potato | 3180 | 150 | 21.2 | 15.9 | 0.9 |

Note:
*N is the layer numbers of the RA rearing boxes in solid feeding.
**The yield of the SW is 5 times as high as that of the MW.

TABLE 4

Calculation of net weigh and volume of the mini space cabin farm in food production for 6 crew.

|  | RA | Terrestrial animal | Chemiculture plants | Aquatic animals & plants | Total |
|---|---|---|---|---|---|
| Volume (m³) | 1.68 | 0.24 | 1.5 | 0.312 | 3.732 |
| Weight (kg) | 84 | 60 | 70 | 312 | 526 |

Introduction to the six kinds of RA are as follow:

I. Housefly Larvae (HFL)—Maggot

1. Overview of HFL

There are many kinds of flies in the world. In this invention we select one type of maggot, larvae of housefly (HFL, *Musca domestica*) as the first candidate. As we know, maggots readily feed on fresh manure and convert residual protein and other nutrients into biomass, which is a high-quality animal feedstuff with rich protein and other nutrients. Due to strong reproduction ability, short life cycle and strong disease resistance, HFL are easily reared in high densities with high efficiency and a little care. It is well known that HFL have the ability to flourish in manure of virtually any animal as well as human. The necessary equipment and techniques are simple. What is more, the techniques are all mature on the ground to feed, process, store, and use HFL as feedstuff for various animals. Therefore, it can be easy to apply these techniques to space mission with a little time and investment.

We do not select HF pupae as our first candidate even though they contain rich nutrition and are easy to harvest. The reason is that there is a loss of biomass in pupal development. Pupae have about half weight of mature maggots and it has larger amount of chitinous exoskeleton, which may reduce nutrient availability.

The weight of one HF egg is around 0.08 mg (one gram of HF eggs contains 12000-14000 eggs), the weight of one adult maggot will be 20~30 mg, which is 250~350 times larger after being reared for 4 days. To date, HFL are second-to-none in producing animal protein 2. Cryopreservation of fly eggs in long duration missions.

We propose to only rear HFL instead of flies in space, because rearing fly in space would take more room and labor than rearing larvae, There is a need to bring adequate fly eggs from earth for food source storage in long term missions. Fly eggs could become HFL after being hatched. HFL mature in 4 days and could become animal feedstuff by producing HFL or HFL powder. Current method for cryopreservation of HL embryos in liquid nitrogen, more than 60% of HF embryos able to develop on the fertile adults. The rate of 60% represents the number of cryopreservation embryos that hatch and go through the larval stages, pupates and then emerges as adults.

We can bring sufficient frozen HFL eggs into space because eggs are small, light and easy to store by freezing. The eggs can maintain their reproduction and growth abilities while frozen for several decades or hundreds of years, just as human semen can survive that long time when frozen. According to our calculations, one astronaut needs about 80 g protein a day, its protein content is equivalent to 130 g HFL powder or about 500 g of fresh HFL (see Table 1). About 1.7 g of eggs is needed to raise 500 g of HFL each day. Thus 6 kg eggs is needed in 10 year for each astronauts. and 36 kg of eggs should be brought from earth for 6 astronauts. If the hatch and survival rate from egg to adult are 60%, it will be calculated as 60 kg HF eggs. This is an acceptable payload to bring into space for 10 years food sources loading.

3. HFL Rearing and Waste Recycling in Space

The feedstuff for HFL in space is very simple, mainly using human and animal wastes (manure), a part of inedible parts of space animal bodies and crops. HFL readily feed on fresh human waste because human waste contains rich nutrition. Most nutrients from all of these wastes can be provided back to the human by taking the food from animals which are fed with HFL. The residues remaining after rearing HFL are odorless and can be used by crop plants as high-grade fertilizer.

(1) The formulation of feedstuff for HFL (weight percent of the feedstuff) is varied on different animals: Fresh human waste (feces and urine) 70% and fresh animal waste (manure and animal body residues): 20%; Residues of space crops (wheat bran, bean dregs, and pieces of crop stalk/leaf): 10%.

(2) Transplanting of the HF egg on the surface of the feedstuff:

The HFL eggs are removed from their liquid nitrogen container in ultra-low-temperature frozen storage, and then warmed for hatching. For a suitable density of feeding HFL, 1 kg feedstuff may be matched with 3 gram of HFL eggs.

(3) Processing of the feedstuff before feeding:

Mixing of above composition in a closed container, humidity of the feedstuff in range of 60-70% (adjusting by the volume of the urine), temperature in 25-30° C., keeping the feedstuff as fresh as possible.

(4) The conditions for rearing:

Serial numbers may be provided on the containers used for rearing HFL. The number depends on the output needs of the HFL. The containers are all closed for gas control. Aeration pipe is installed in both the upper and middle layers for good aeration and oxygenation, and to keep the aeration speed of 1 grade. The gas flowing in the aeration pipe will be filtrated by the deodorizer. The feedstuff is stirred once a day to avoid overheating and internal oxygen shortages after placing fly eggs in the feedstuff. Before rearing, the feedstuff and containers should be placed in a microwave oven for bactericidal processing. The interior of the containers should be maintained in darkness.

(5) The structure of the containers and the rearing procedure:

Each container's volume is 40×50×10 cm³. It is much smaller than that on earth because in microgravity, HFL and feedstuff have to closely touch in order to keep feeding all the time. Usually, 1 kg of mature FHL can be produced within one rearing cycle of 3.5~4.0 days for each container. The container is divided by three layers with thickness of 6 cm and 2 cm and 1 cm respectively. The upper layer is 6 cm thick for HFL rearing only. It is full of feedstuff. The middle layer with a thickness of 2 cm contains wet wheat bran or bean dregs for decontaminating the viscera of the HFL after 3.5 days of rearing. The lower layer with a thickness of 1 cm contains wet wood bits or silver sand for making the mature HFL hungry, collecting and cleaning the mature HFL. There are two mesh screens between the three layers. The HFL skin can be cleaned while it goes through the tight screen opening.

The HFL can be driven to middle and lower layers by strong lighting on the surface of the layer and can stay in both of the layers for 3-4 hours respectively. They can then be collected in the lower layer after 3.5 days of rearing. Do not take more than 4 days as the collecting time, as this is considered to be the maximum biomass harvest for HFL to prevent any HFL from becoming pupa. After rearing HFL, all the residue, which consists of water and useful contents, can be recycled as fertilizer for space crop plants.

4. The tests for rearing HFL by feeding the manure: In our 60 quails feeding test with HFL, the daily manure of two adult men and 60 quails, with adding 10% manure weight (250 g) of wheat bran as the feedstuff for rearing 2.5 g of HFL eggs, can harvest around 618 g fresh HFL every day. It is enough for feeding these 60 quails with HFL as the protein feed every day.

5 Rearing HF in Space.

Fly rearing and reproduction could be a standby method for sudden use in long term missions. Moreover, it is easier to rear HFL than HF in space, so a great deal of breeding space, labor and expense for rearing flies can be saved. In normal situations, there is no need to rear flies on long term missions because the problem of storage of HF eggs has been solved. But when a contingency happens upon losing eggs, the crew can rear HF to make up for the lost eggs. Therefore the technology of rearing houseflies should be reserved. Rearing HF in space will be taken into consideration in the following points:

(1) Selecting of fly eggs: for assuring satisfactory egg quality, to choose the pupa more than 18 mg in weight as the best seed, and the fly eggs gathering will be done between 6-10 days of ovipositing.

(2) Rearing quantity and density. The rearing density of HFL on the ground in large scale is 40000-60000/m$^3$, but in space, where the crew only needs to rear a small number of flies for egg collection, flies can be reared in a cage with a size of 40×40×40 cm$^3$. It is a closed cage possessing four mesh walls for aeration. For one fly, its minimum active range is 10 cm$^3$, so around 6000 of flies can be reared in one cage. In this cage, around 15 gram eggs can be laid every day. This is sufficient for the food source demand of 5-10 astronauts a day. (one astronaut needs 1.5 gram fly eggs as the daily food source)

(3) Feedstuff:

The feedstuff of ovipositing HF is required to be better than that of HFL, because HF like to eat HFL paste (smash live HFL into paste), and fortunately, the HFL paste could be easily produced self-sufficiently in space. A formula for the feedstuff for HF in space is 70% of HFL paste and 30% of wheat bran or bean dregs.

(4) Approach for Rearing FL in Space:

HFL may be reared as mentioned above. Before HFL reach maturity, they usually take 4 days of rearing.

The HFL are all in the lower layer of the rearing container with wood bits for pupating, at a temperature within 25~30° C. and humidity of 60~70%, kept in the dark with an aeration speed of 0.5~1.0 grade. Pupa will have eclosion after 5-7 days, while HF can oviposit 3 days after eclosion and the ovipositing period is 30 days or so. As a rule, HF will be killed after 15 days of ovipositing and egg gathering will be terminated to assure satisfactory egg quality.

The rearing temperature in the HF rearing cage is 25~30° C., the humidity is 60~70%. The feedstuff for rearing HFL is supplied using a small feedstuff tray in the cage, including a sponge saturated with water, a feedstuff sponge and a oviposition-luring sponge (water and feedstuff are absorbed onto sponge to prevent them from floating off under the microgravity). In addition to fresh human feces as oviposition-luring matter paste on, the feedstuff is applied on the oviposition-luring sponge, which can be put into 3 days after eclosion of pupa, at intervals of 12 hours. These three sponges should be alternated and the HF eggs could be collected once every morning and afternoon. The rearing cage needs to be sterilized with ultraviolet ray before rearing. HF pupa should be disinfected by using potassium permanganate before eclosion. Rearing HF requires lighting. Longer lighting times provide greater benefits for FL growth and ovipositing.

6 Processing of HFL powder (1) Steps: Collecting Fresh HFL→Cleaning→Drying→Grinding→bactericidal procedure→Collecting powder→Package→Storage (2) Drying: Microwave under 80° C.

(3) Drying within 6 hours after collecting HFL to prevent fresh HFL from becoming pupa.

(4) The HFL powder can be stored by freezing for long term preservation.

7 Application of HFL as feedstuff for animals:

Due to the rich protein and other nutrition that HFL contain, applying HFL as feedstuff provides good animal protein and other rich nutrients to poultry, livestock and aquatics to achieve high rate of reproduction and survival.

II. Mealworm (MW):

Originally, it is a kind of pest living in the warehouse. similar with the musca, it experiences four stages: ovum, larva, pupa and imago in its life, and has a 29-35 mm body length at its mature larva stage. The reasons for selecting it as the second RA are as follows:

1. The feeding habit of its imago and larva is wide and various and the requirement for the feed is low. It can digest and recycle nearly all bio-wastes in the space that can not be eaten by HFL. Besides all kinds of cereal, wheat flour, rice flour, wheat bran, dried potatos and their detritus, it also eat bread, biscuit, feather, oil, dried fish, dried meat and insect corpse, rat dung, vegetable leaf, fruit and some moldy stored goods. In the artificial feeding, besides the seed and subsidiary products of various graminaceous crops such as wheat, barley, corn, sorghum, chestnuts, paddy, the subsidiary products such as wheat bran, rice bran, maize peel, the organic wastes dominated by the crop straw (wheat straw, rice straw, and corn and sorghum straw, and so on) can also be used as the feed after fermentation, which can make the ratio of insect to feed reach 1:3. In addition, the green succulent feed, including various vegetable stems and leaves, fruit peels, and trees and grasses, can be used as feed of MW. MW can eat and digest organic plastic, and the indigested plastic component in MW manure is quite less. One kg organic foam plastic and some fresh vegetable peel can make MW increase above 3 kg; MW can grow and propagate normally after eating organic plastic, and it is deemed that there is certain active substance that enable MW to digest organic plastic, and such ability can be developed and reinforced in artificial conditions. It has being proved that of plastic component is extremely less in the manure of the MW, which neither generating static absorption, nor burn, nor float, and keeping putrefactive odor, thus a new effective way for treating of the white pollution was issued, and a lot of organic plastic packaging waste can be converted into precious high protein and high nutrition food source in the space at the same time. We tested by using HFL manure with cabbage peel to raise MW. It is found that MW also likes eating HFL manure, and increases weight obviously.

2. MW has quite rich nutrition, which is a RA with high protein, high fat and relatively complete amino acid content, particularly high protein content. It contains 8 essential amino acids (in Table 2) that can not be synthesized in human body, among which four kinds exceed mode value recommended by FAO/WHO. And its total amount of essential amino acids is higher than that of pork, mutton and soybean, close to that of beef and fish. The ratio between its saturated fatty acid and unsaturated fatty acid is close to fatty acid of fish. It also contains various rich vitamins, minerals and microelements. Its 90% organisms can be used as feed and food, and the wastes are less. The protein content and fat content can be up to 80%, which can be called as an improved type for super farming, which is not only used for feeding edible animals, and also for producing animal proteins, to directly provide healthy foods for human.

3. The practice proves that MW is a high quality fresh bait, which has been widely applied in feeding all omnivorous small animals, such as poultry, birds, aquatic and amphibian animals. It has good palatability, complete nutrition, and convenient for feeding. Of course, it is particularly applicable for feeding 3 animals in this project. MW paste has remarkable-feed inducing effect to tilapia, and the effect is best by adding 2% MW paste as baiting 4. The frass of MW is the high quality fertilizer for growing plant, in which the crude protein content is up to 24%, and further it contains nitrogen 3.37%, phosphorus 1.04% and potassium 1.4% as well trace element such as zinc, boron, manganese, magnesium, copper, etc. It is a high quality organic fertilizer, also can be used as crude feed for poultry and livestock. Its manure is dry, without exotic smell and with small size. It can be easily stored and transported, and fast matured, occupies no site and is very convenient in use. Its composite fertility is greatly better than that of any fertilizer and farm manure. It has quite high natural porosity and tiny particle structure, with micro-film formed on the surface by exudate from the enteron of MW, which is good for improving the oxygen content in the soil. Used as the plant fertilizer, its fertility is stable and lasting, and it can improve the soil activity.

5. The imago is good at climbing but can not fly, therefore, the imago is unable to escape so long as the inner wall of the feeding box is smooth.

6. It has strong vitality, capable of resisting hunger, cold and dryness; it can even survive in low temperature without having anything for over 6 months. Usually, it is no need to supply water; only having the vegetable leaves and peels with water can satisfy its water requirement. Feed the larva once at every 2-3 days during the breeding. It is very quite, requiring no special care.

7. It has strong reproduction capacity, the male worm is able to mate with eight female worms successively without any impact to its life span and fertility rate. When the moisture and temperature of the feed are appropriate, every female worm can lay egg up to 580, and the eggs would be incubated in 3-7 days. The larval phase is 90-120 days; the pupal phase is 6-8 days; and the average life span of imago is 60 days. It can reproduce in space environment without any limit. The imago can not fly as HF does, so it is unnecessary to treat like the fly egg: to be frozen in cryopreservation and brought to the space from the earth in this invention.

8. At average, the yield of every square meter within 90 days is up to 5 kg (it takes about 90 days from egg incubation and growing into imago). They move and take food together. As like HFL, it can be bred in feeding box. The dimension of feeding box shall be the same as that of HFL feeding box. The feeding box can also be piled up to realize the solid feeding, therefore, the yield in every cubic meter should be 5N kg (N refers to the floors of the stacked feeding box).

9. Its pupa is an exarate pupa, without frass inside the body. The food made from it is delicious and rich in nutrition. It can be baked or made into fried "lobster" for direct eating, also can be made into food with high protein, which is mainly the food made from the protein and amino acid extracted from MW.

III. Superworm (SW)

SW is a new protein insect recently introduced to China from Southeast Asian countries, the coordinal but heterogenous insect to MW. They are similar in the appearance. Its food habit, reproduction characteristics, growth period and rate are also quite similar to MW. The female worm is able to lay 600-1000 eggs successively until it dies. However, SW has larger body: the larva is up to 7-8 cm long, and the mature larva is 5-6 mm wide, which is 2-3 times larger than that of MW; a single worm is 1.3-1.5 g. It has higher nutritive value than MW. As Finke reported, it tops in the weight, content of protein, methionine and energy as compared to HFL, MW, crickets, silkworms, waxworms, etc. In addition, it has more kinds and high content of trace element, being a very important protein insect. It is clear that its development potential is greater than MW, and its yield is five times of that of MW which earns it another name as super bread insect. It can be bred constantly days and nights in the same piled feeding box and in the same cabin or room as HFL, MW, and EW. It takes about 90 days from the egg incubation to growing into imago. The average yield of every cubic meter within 90 days should be 25N kg (N refers to the floors of piled feeding boxes). As it is introduced just for a short time, the relevant research information and data are less. We choose SW as the third RA in circulating bio-waste due to its good development potential, and its introduction will increase the security of the entire food production chain in the space.

IV. Tubifex (TUB)

It is a most common fresh water zoobenthos. Its reproduction capacity is strong and the growth is fast. In the reproduction peak time, the daily multiplication rate is twice as that of species just introduced. It is a hermaphrodite but allogamous. It can reproduce in all seasons. When the water temperature is between 28-32° C., the reproduction is the fastest and the hatchability is the highest. It favors living in dark micro-flow zone with mud. It takes in the mud and then discharges it, which is good for changing the underwater circumstance. Its food habit is extensive and various, taking in mud as well as detritus, germ, alga and meiofauna. The hatchling larva is 0.6 cm long and will grow into imago in 1-2 months. Usually, the harvesting will be done one month after the species introduction. It takes two months to become sexual maturity. The life span of those bred by artificial propagation is about 80 days, and the body is 5-6 cm long. Its regeneration capacity is very strong, and can grow into two whole individuals when being cut into halves. Generally, the daily yield per square meter is approximately 500 g just after 30 days of the species introduction. It is rich in nutrition with protein content of above 70% when dried and the complete amino acids, and therefore a living bait for fishes. The TUB in this project is mainly placed in the flow filter tank at the downstream outlet of the tilapia breeding water tank. The fish feces and other biofertilizer are the feed for TUB, so as to purify the water. And its organism further is the best feed for fishes.

V. Cladoceran (CLA)

The various zooplanktons bred in the sewage water pool and river, as the common name for Cladoceran and Copepoda. The protein of CLA contains all the necessary amino acids for aquarium fish, and the content is far higher than that of other common feed, accordingly it is a good natural feed for fish. CLA is seasonally reproduced and grows fast. It is sensitive to light. We introduce CLA as an auxiliary recycling animal for water purification function of TUB.

VI. Earthwaorm (EW)

EW likes to live in warm, wet, tranquil and dark soil where rich of organic matter. EW is an omnivorous scavenger, with various feed, including the germ, yeast, protozoa, eelworms, the bodies of animals and plants as well as the feces of the livestock. The feed for artificial breeding of EW includes excrement and bodies of animals, straw of crops, starch, glucide, garbages, grasses, tree bark, fruit peels and vegetable leaves, which should be fermented and fully decomposed for easy absorption. Therefore these piling organic matters will be free of bad smell.

The annual yield of EW in every cubic meter of manure is about 40 kg, and that in every cubic meter of plants organic matter is 12 kg. Artificial breeding of EW is a good way to provide live bait for fish and high-quality protein at present.

We introduce EW as the sixth RA in recycling of bio-waste. EW is bred in the planting soil of terraneous plant for improving the soil quality and recycling the manure of MW and SW as well as the waste of animal and plant which has not been recycled by the previous terraneous RA, and then EW is fed to the EA as live feed which is rich in nutrition.

Part Two: Edible Animal (EA) System:

1. The Reasons for Introducing EA:

Here the animal husbandry of six RA are extremely rich in nutrients, in combination with the space plants for direct human consumption, should be very simple and ideal. Recommended in particular is the pupae of the MW and SW which are naked pupae without the pupa shell outside and without the frass inside the body. Their larvae do not eat feces as directly as maggot, therefore, they impress people much better and is more easily acceptable as food than maggot. Roasted them in the microwave oven for a few minutes and then added a bit of salt to MW and SW pupae will be very delicious similar to roasted shrimp. At present, the food industry to develop them to a variety sauce and food additives, etc., is no longer a minority. However, people's cultural values and food habits made it difficult to accept insects as food, not to mention keeping their own feces for feeding maggot as the food.

Therefore, this invention completes the key first step: breed RA to converse the excrement of human and animal, the entire bio-waste from animals and plants into the RA biomass with high nutritive value. The second step is to make these RA as the feed of EA, and then to make food from the bred EA for space human. The EA bred in the space includes two kinds: aquatic and terrestrial kinds. We only choose the poultry, aquatic animals and amphibians in light of the limited cabin in the spacecraft and space station, for example, Quail, Tilapia, Apple Snail, loach and Rana catesbeian. In the future, large aquatic and terrestrial animals can be bred for producing milk and goat's milk in the planet immigrant bases.

2. The reasons to choose the above several small EA as the space-breeding animals are that they have followings in common:

(1) The feed is self-sufficient in the space. They all favors the above six live RA or feed made from RA powder and use various inedible plants as other auxiliary feeds. These EA can be fed with germ, algae or RA powder and wheat bran in their baby phase, such as baby quail, fish, snail and tadpole and with live RA and inedible plants in the adult phase.

(2) They all have been undergone preliminary incubation and breeding experiments in the space, although only for testing on the ecological purposes and not for the food production, it still proves the feasibility to breed them in the space. In February 1999, the astronauts in Russia Peace Space Station helped to incubate 37 baby quails from 60 quail eggs, and 10 quails survived under the severe environment of strong radiation in space. On the USA STS-47 space shuttle, an embryological study on the frogs brought from the Southern Africa was carried out. These frogs laid eggs in the space, and all the eggs gave birth to tadpole. The ecological experiment of spawn-to-spawn was carried out successfully on fish and silkworm: spawn laying, incubation, growth and spawn laying.

(3) Their spawns (quail's egg, roe and frog spawn) can be brought from the earth. They can be preserved in liquid nitrogen under extremely low temperature for a long time and can be incubated when the temperature returns to normal later and the offspring will grow to adult and lay eggs/spawns. They also can reproduce and lay egg in the space by themselves.

(4) They are all small in the bodies, grow fast and have short growth period. Their food habit is various, and the conversion rate of feed vs meat is high. They have short sexual maturity period and large laying, strong adaptability and disease resistance, suitable to high-density feed. These animals itself and their eggs are food with low fat and cholesterol but high protein, very delicious and easily digested.

(5) The breeding technology for these animals on the earth is mature, and the equipment is also simple.

3. Reason to choose small aquatic animals:

(1) One outstanding advantage to breed aquatic animals is that they originally live in the water and is adaptive for the water environment similar to the microgravity environment in the space. Therefore, their lifeway in the space, in particular food taking, growth and reproduction, will not be influenced by microgravity environment.

(2) These RA can survive in the water for a certain time, for instance, the HFL can survive and move about in the water for over 24 hours, in this way, it is convenient for the aquatic animals to eat these live RA, just like on the earth.

(3) It is discovered recently that large quantity of water ice likely exists on the Mars and the moon. Once the water ice is developed some day, there will be no limit to the water source for breeding the aquatic animals with these RA on these planets, and various aquatic animals can be massively produced for providing food necessary for planet immigrants. Even in the spacecraft and space station with limited cabin volume, the aquatic animals can also be bred in the same way as the aquatic animals are bred in high density and the volume of the circulating water tank is limited.

Introduction of the three Edible Animals (EA):

1. Quail: The kind of meat-egg quail will be selected as the samples.

Besides the above common characteristics, this kind of quail usually lays egg 35-45 days after incubation with laying rate of over 80%. The proportion between the egg and weight of quail is 2.5-2.7 times of that of hen. Quail eats a little, with the proportion between feed and egg being 3:1; quail likes live RA, and its excrement and inedible part of its body are the feed for those six RA. We take the daily excrement of two adult human and 60 quails as well as 250 g wheat bran for breeding HFL, and use the 618 g fresh HFL harvested every day to feed the 60 quails with obviously higher average weight (130%), egg weight (110%), and laying rate (257%) than that of control group fed by common feed.

2. Tilapia: There are many kinds of tilapias, here we take tilapia nilotica as a feeding sample.

(1) It is characterized of varied feed habit, fast individual growth, large individual body, strong disease resistance and reproduction capacity and delicious meat. Strong ability for grabbing feed. Tilapia has very high feed utilization rate. Its feed includes septic dross, tailing, algae, protozoan and Cladocera. The bio-wastes and RA biomass in the space are the optimal feed for tilapia since tilapia has very wide food range and strong digesting capacity. The minimal converting rate of feed vs biomass is 1.1, i.e. 1.1 kg feed can produce 1 kg fish.

(2). Tilapia is a fish resistant to low oxygen content; the water temperature most suitable for tilapia grow is 28-35° C. It has strong adaptability, easily cultured and not susceptible to disease, and with high mass yield and production potential. It is an ideal fish bred in net cage and in running water. The yield in every cubic meter of the net cage can be up to 30-40 kg per year. Its energy production capacity in the net cage is 130 times higher than that of in the pool.

(3) Reproduction of the tilapia; it takes 3-6 months for growing into sexual maturity. A female fish of 150 g carries about 1300-1800 mature roes. The amazing thing is its incubation in the mouth, the oosperm is contained in the oral cavity of the female fish in the incubation which usually takes 5-6 days and after the incubation, the female fish often protect the fingerling in the oral cavity for 15 days or more. The particular incubation in the mouth ensures the reliability of self-reproduction of tilapia in the space environment.

3. Apple Snail: It is a large freshwater snail introduced from Amazon river basin, South America. With high protein, and Vitamin C and carotene, it is an ideal tonic product as well as animal substitute for fish meal and animal feed source with high protein.

(1) It has great adaptability in shallow water pool, stream, slot, even the medium and small sized water region severely polluted by the factory;

(2) It is an omnivorous animal easily controlled. The plant feed such as vegetable leaves, grasses, peanut bran, wheat bran, and animal feed such as dead fowls, beasts, fish and waster materials of slaughter houses can be used for breeding Apple Snails; therefore, the bio-waste and RA biomass in the space are its best feed;

(3). Large individual body, fast growth and high yield Usually, the young snail can grow to 200-250 g under a better breeding environment for half year, and the largest individual body will reach 400-500 g; at average, the yield in every cubic meter can be up 7.5 kg every year;

(4) Strong reproduction capacity: the snail can lay spawn for the first time after 4 months' breeding, with 1000 spawns at least; the baby snail will be incubated about one week after the laying.

(5). High-quality meat: the meat is golden, crispy and delicious, with high nutritive value. This snail is free of pathogen and carcinogen. However, as apple snail has too strong reproduction capacity, and will eat the crop, it is only used as the bait feed of high quality in some region at present.

(6). Apple snail likes to stay in shade and is sensitive to light; it seldom moves about in the day time but frequently at night; the most suitable water temperature for it is 25-32° C. The young snail can usually grow to about 25 g, 50 g, and 100-150 g one month, two months and three months after the spawning respectively. The young snail can be bred in cement tank or vat.

Part Three: Plant System, Including Terrestrial and Aquatic Types

The terrestrial plant includes crop and vegetable: The crop include rice, wheat, potato, sweet potato, soy bean and the vegetable include green-leaves vegetable, broccoli, garden peas, brassicas tomato etc.; edible fungus (requiring no photosynthesis, the fungus can be taken from the earth after it is frozen in extreme low temperature). To overcome the adverse effect of microgravity in space on the plant growth, it is better to grow in water. The terrestrial plant system is applicable to part gravity environment in the planet immigrant base. As for the microgravity environment of spacecraft and space station, due to their limited cabin space, it is difficult to grow terrestrial plant to provide food for human.

Aquatic plant: same as breeding of aquatic animals in the space environment. It is better to adopt the aquatic plant system so as to completely overcome the adverse effect of the microgravity environment on the absorption function of plant's root. *Pistia stratiotes, eichornia crassipes* and *lemmaminors* are all ideal aquatic plants for growing in microgravity environment. However, these aquatic plants can only be used as the feed of EA and RA, human can not eat them directly. The rice used to grow in water, and green-leaves vegetables, sweet potatos and potatos can be planted in water too. In addition, there are algae and germ: algae can be *spirulina platensis, chlorella vulgaris*, etc. which can adopt urine as the culture agent; the germ can be photosynthetic germ;

The culture technology of *Nostoc sphaeroides* kutzing (KT in brief) is also recommendable. KT is a lower unicellular cyanophytn, originated from a rice field in a mountainous area in Hefeng County, Hubei, China. It has a history of more than 1500 years for keeping the KT as a healthy food in China. The KT can absorb $N_2$ and $CO_2$ in the water to convert them to be biomass with high protein and amylase effectively, its high nutrition biomass can be human's food directly, and release the $O_2$ for aquatic animals needs.

Through the research and development of Wuhan Institution of Aquatic Organism, Chinese Academy of Science and other units for years, the KT has realized the indoor cultivation in water tank, and mature production technology is formed, and the average and highest biomass yield of KT can reach 1569 and 5354 g/·$m^3$ d of its fresh substance cultured out-door in a grass water tank with 40 L volume. Its status and taste is similar with cooked pearly dumplings made of glutinous rice flour, but its nutritious value is much higher than that of rice. According to the opinion of the algae expert in the institution, KT has very high nutritious value and includes high content of proteins and amylose, 8 amino acids necessary for the human body, and other active substances. The KT fresh substance is just like gorgeous pearl with three colors of black, blue and green, and very delicious and can be directly eaten by human without any food processing. It can be continuously cultivated and the cultivated water will keep free of contamination. Thus it is very ideal to apply this technology to the-aquatic ecological growth system of such project.

Part Four: Spaceman

For role in this food chain, the spaceman is the food consumer and the main producer of the biological wastes.

Implementation of Mini-Farm in the Space:

It includes two cases, microgravity environment and low-gravity system. The former is mainly for spacecraft and space station and the latter mainly for the space immigration bases of moon and Mars and so on.

The difference between them is that the former one has stricter requirement for the volume and weight of the farm in the space. The RA system designed in such system is applicable to the both cases. In the former case, the aquatic animals and plants are cultivated mainly by adopting the closed circulation water tank system, the aquatic animals mainly refers to fish and snails, the aquatic plant is algae; for the terrestrial animals, we mainly breed quail, and the terrestrial plants is mainly cultivated with water-growing method. The latter case has less limitation on volume and weight. In addition, many evidences appear that there are lots of water ice existing on the moon and the Mars, and the partial gravity has small influence on animals and plants ecologically, so the various choice for animals and plants will be more diversified, the terrestrial organism system and aquatic animal/plant system both can be developed in scale either big or small. Here, we mainly introduce the implementation of mini-farm in the space under the microgravity environment. Because RA, animals, and plants all have the growth environment temperature of 25-30° C. and relative humidity of 60-70%, so they can be fed and cultivated in the same cabin.

1. RA system: Except that TUB and CLA are cultivated in a very small water filtering tank, other four kinds of RA are placed in the plastic boxes or wooden boxes in the same size. Each box has the area of 0.2 $m^2$ and the volume of 0.02 $m^3$ (inner diameter of 50×40×10 cm) and the weight (including RA and feedstuff) of each box is 1 kg averagely. All of these boxes can be piled for solid cultivation. According to our FHL-feeding test, fresh FHL of 618 g can be obtained from the dejecta of two adults and sixty quails. It is calculated that the fresh FHL can be produced at rate of 1 $kg/m^2$.d and that 3 cultivation boxes will be sufficient for each day, and that 12 boxes will be needed for continuous four days. The box amount for other MW, SW and EW will be determined by the quantity of the biological wastes. In addition, in order to prevent the mutual killing of MW and SW in different growth stage, it is required to carry out cultivation in a staged manner. We totally use 12 boxes based on 3 stages, and 4 boxes are needed for each stage and two boxes are used for feeding each of MW and SW. 4 boxes are required for EW cultivation, thus there are 28 boxes totally. So, the bio-waste of two people can be treated by using these RA in a cabin space of 0.56 $m^3$, with the weight of 28 kg. In the case of six people, 84 boxes totally and the cabin space of 1.68. $m^3$ will be needed with the weight of 84 kg. The cabin volume and weight covered by the boxes are very limited, and also it is easy to conduct such arrangement in the spacecraft and the space station. With such small volume and weight, these RA can efficiently make all the bio-wastes to be the biological biomass with high protein and high nutrition. Because all of them are fed in a heap with a high density and they are closely contacted with the feedstuff, each box can additionally provided with the aerated and light-proof cover for covering the feedstuff, and is fixed on the bulkhead bracket. RA will not be "space floated" under the microgravity environment. So it is guaranteed that the food-taking and propagation environment of RA will not be affected. Other attached devices are very simple, such as egg-laying boxes, fly-feeding boxes and separating mesh screens which are all portable and only cover a little volume and weight.

2. EA system: For terrestrial animal, we only recommend quail at present. It will grow well by mainly taking the above-mentioned RA as its feedstuff under the ground gravity environment. The quail can be cultivated in the high-density manner, so the space needed is limited. Sixty quail are fed in the cage of 100×80×10 cm, namely 0.08 $m^3$ equal to the volume of 5 worm boxes. Quail eggs of 500 g can be obtained every day based on the laying rate of 80%. This is sufficient for the daily protein demand of two adults. In case of producing the quail eggs needed for six people, it will be required to use 3 cages to feed 180 quails, covering the volume of 0.24 $m^3$ The maximum weight of the cages and quails is about 60 kg.

However, the quails cultivated in the space station cabin by Russia, especially the small squab quails, can not be adapted to the microgravity environment and huddle together, their normal food-taking were affected. Therefore, the Russian scientists proposed making one waistcoat for each quail to fix them. But it is inconvenient for them to take food. So, it is very important to solve the problem that the quail can freely move in the cage without being floated and reversed, and it will solve the food-taking and mating and propagation problems for the quail in such method.

3. Plant system: The terrestrial plant will mainly be cultivated in chemiculture, and we will mainly plant the crops including rice, sweet potato, potato, soy bean and so on, the vegetables of green-leaf vegetable (such as broccoli, garden peas, brassicas), tomato, carrot and so on, and the edible mushrooms. All these plants are edible for human. In addition, water lettuce, hyacinth or water peanut can also be planted for feeding RA and aquatic animal. Except for edible mushrooms, the plants all need the lamp light for photosynthesis. The requirement of realizing photosynthesis can be achieved by using lots of light emitting diodes which cover almost no space and weight. Nutrition for the root of the plants can be provided with nutrient fluid in slow circulation soaked into spongy. So, chemiculture also can realize solid cultivation by using the planting water tray. The water body for planting water tray of 1 $m^2$ is designed to be 5 liters (L) volume averagely and the planting area of 10 $m^2$ will need water 50 L, in addition, the weight of the 10 trays and plants will be 20 kg, so total weight is 70 kg. If the plant height in each planting plate is 15 cm, the cabin volume of 1.5 m' will be needed.

Figure 2:
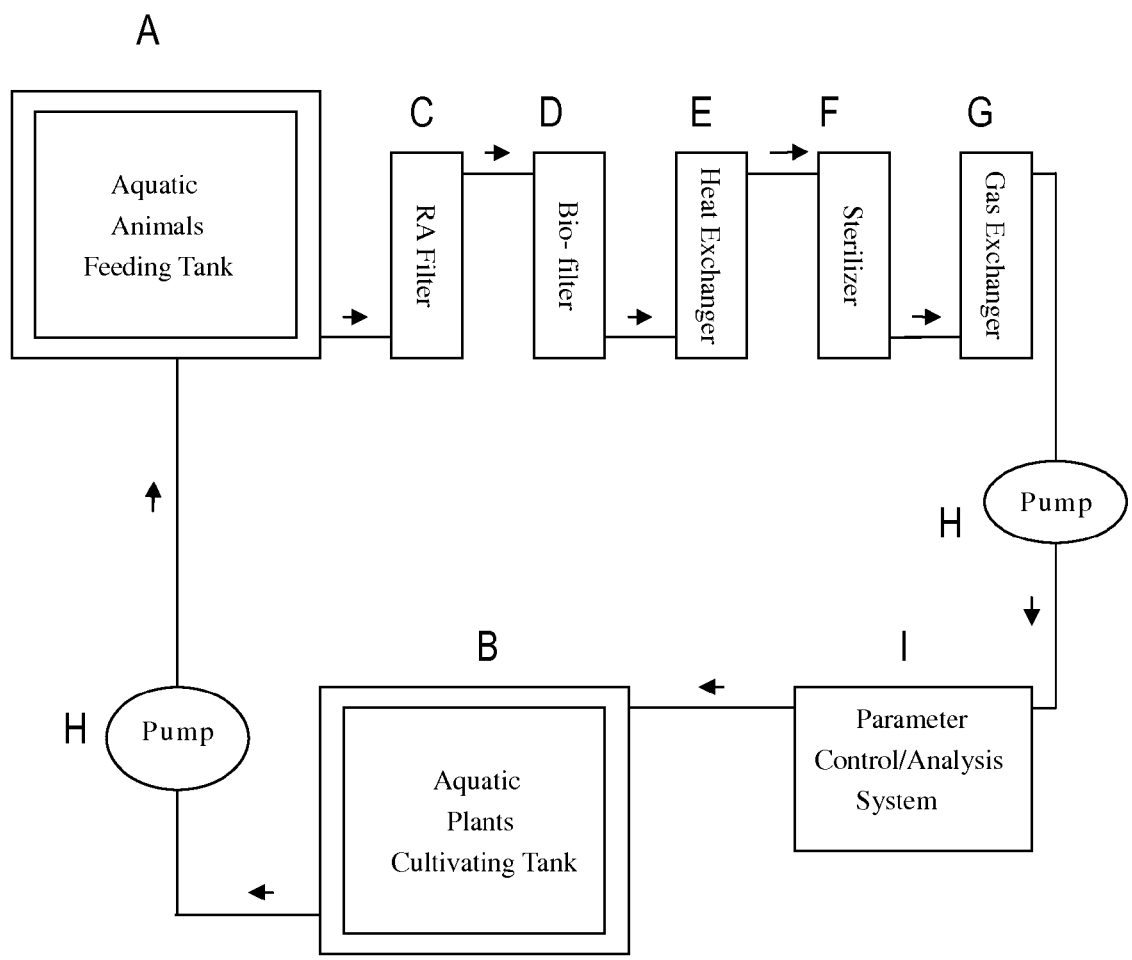
FIG. 2: The structural principle of cultivating aquatic animals and plants in the circulating water tanks ecosystem

4. Ecological cultivation system of aquatic animals and plants:

The ecological cultivation system of aquatic animals and plants designed in this project is shown in FIG. 2, it is supported by RA which as the feedstuff for the aquatic EA or as the wastes recycling function.

A. Aquatic Animal tank: The tilapias and apple snails will be bred in the closed water tank, and loach is used as the standby animal. Their feedstuff mainly includes all kinds of fed fresh RA and the stems and leaves of the plants. Their juvenile fish and snails will be fed with CLA, RA powder, diatom, bacteria and plant by-products of wheat bran and so on. The water body has the volume of 50 L, with 50 fish and 50 snails fed in it.

B. Aquatic plants tank: Algae (mainly KT) and the aquatic plants are cultivated in the closed plant cultivation water tank, which can purify the water and absorb $CO_2$, and release $O_2$ through the photosynthesis. Their organisms can be directly eaten by human or used as the feedstuff of the aquatic animals. The capacity of the water body is designed to take 50 L as one unit.

C. RA Filter is the filtrating tank with 2 L water body and used for cultivating TUB and CLA. It is connected with the outlet of the animal-feeding water tank and can filter the animal wastes. Bio-wastes from the animal tank through the mesh screen will be used as the feedstuff of TUB and CLA.

D. The biological filter is the water tank with 2 L water body and used for cultivating the photosynthetic bacteria and diatom, they can reduce the sulfured hydrogen, ammonia and nitrogen content in the water under the weak light condition, so as to purify the water and become the feedstuff of aquatic animals. In addition, they can prevent the diseases of aquatic animals, and promote the fish growth and survival rate.

E. The heat exchanger is used to provide and control the water temperature of such cultivation system, with heat source provided by electrical heater, so as to make the system maintain to be in the temperature range of 25-30° C. which is the best growth temperature for all of the animals and plants.

F. The sterilizer: killing the baleful bacteria and microorganism.

G. The gas exchanger: is used to regulate the content of oxygen, $CO_2$, ammonia gas, nitrogen and other important gases in the water body.

H. The pumps: the water pump is used to guarantee the water circulation power and normal flow of the system.

I. Parameter control analysis, monitoring and, recording system: It is connected with all the sensors and can automatically record and regulate all the parameters including light, heat, water flow, oxygen, nitrogen, ammonia, sulfur, PH, $CO_2$, germ and so on to make them maintained in the normal scope. Light emitting diodes are used to provide the light source.

One system has the water body of 104 L and the whole system is 104 kg weigh, with the volume 0.104 $m^3$ In case 3 systems are used, the total weight will be 312 kg, with volume of 0.312 $m^3$.

5. Estimating calculation on net weigh and net volume of the cabin-type mini space farm used for food regeneration for 6 people The estimating calculation on the total weight and volume covering in the cabin of the food regeneration system for 6 people is shown in table 4. It can be indicated that the net volume for the mini-farm in the cabin is 3.732 $m^3$, and the net payload is 526 kg. If the attached devices and operation space is taken into consideration, the covering area in the cabin will be doubled and about 7 $m^3$, and the weight will be increased by 30% and 700 kg. This is acceptable for the spacecraft and space station of the manned space exploration. Due to up to date, it is difficult to estimate the real sorts and quantities of the biological wastes in the space living environment, so this estimating weight and volume for mini space farm is just a demonstrable sample.

Such system can provide spacemen with the food list as follows: The edible RA, quail and its eggs, tilapias, apple snails, loaches, KT, sweet potatos, potatos, soy beans, the vegetables of green-leaves vegetables, broccolis, garden peas, brassicas, carrots and so on, and edible mushrooms.

Other Functions of Maggot, MW and SW:

Due to lack of protection from the earth's atmosphere and magnetic field in space, there are harmful effects on the human body due to strong space radiation when humans live in space. These effects include a reduction in the number of white blood cells and immune cells, cancer, damage to fertility, etc. The desire to resist the harmful effects of space radiation has lead to research programs at NASA and in many countries of the world, but to date no effective way to overcome these effects has been developed.

Tests have proved that eating maggot powder as a healthy food, can improve the ability of animals and humans to resists harmful radiation and immune function effects. For patients under treatment using radiation or chemical therapies, the reduction of white cells and immune cells obviously slows down and hair lost is apparently decreased. The ingredient in maggot bodies that provides these functions is not certain, but there is a significant clinical effect for humans living in space or on earth. Crops or animal internal organs could serve as feedstuff for rearing maggots on earth or in space, some herbal medicines and other ingredients with special function can be added in those feedstuff, or into maggot (pupa) powder for increased effect. These can also be taken by the people who are exposed to radiation or live in locations that are polluted by radiation. Furthermore, animals that feed on maggots, their meat, egg and milk can experience similar benefits.

The same situation, tests have proved that eating the powder or the bodies of MW, SW, and their pupa as health food can reduce of the level of the blood lipids and cholesterol effectively, thus improve human's cardiac vascular function and cure the hyperlipidemia. Furthermore, the animals that feed on MW, SW and their pupa, the animal meat, egg and milk can experience similar benefits.

Maggots, MW and SW can also be used as carriers for special ingredients by feeding them with relevant ingredients that humans need, such as vitamins, minerals, electrolytes, antibiotic and some herbal medicines etc. With this approach, the animals reared on the maggots, MW, SW will serve as carriers for the relevant ingredients by virtue of being fed on the maggots, MW and SW.

The Characteristics of this Invention:

1. Six kinds of RA are fed in the space and form the closed-loop ecological food production chain together with the selected EA and plants, which can realize to recycle all the biological wastes in the human living space environment and convert the biological wastes to high-nutrition food source. Therefore, it is likely to realize the self-support of the food in the long term space missions.

2. These RA have the capacity of converting the bio-wastes efficiently and can be continuously fed in the solid manner. In addition, they need the least energy, manpower and equipment, and make it possible to build the mini space farm at the minimum area, volume and weight.

3. This system can perfectly realize recycling of the food and the partial water and air of the life support system.

4. These RA can provide balanced and rich nutrition needed for human body and EA, such as rich protein, amine acids, fatty acids, amyloses, vitamins, mineral compositions, trace elements, and many unknown nutrition elements. The RA together with the EA and plants, can meet the all kinds of nutrition requirements of the animals, plants and the human living in the space for long term.

5. The eggs of these RA and the EA can be stored in liquid nitrogen for long term and also can be hatched later by restoring the temperature and then grow, which solves the problem of long-term storage of the food source.

6. These RA, EA and plants have very strong vitality, very short growth cycle, and very high yield. They can be continuously cultivated in high-density manner at all hours so as to realize the high-efficiency food production in the space.

7. The animals and plants production process of the whole system is not related with any chemical substance and can not produce harmful substances or pollute the environment. The protein powder processing of these animal bodies is also free of bacteria and chemical substances, so it is safe to use such protein powder to feed the animals and directly to eat it by human. Therefore, it is actually green, ecological, environment-friendly and efficient agriculture.

8. rearing these RA, EA and plants are all the mature technologies on the earth, and based on this, it will take less investment and time when conducting such rearing in the space. Only simple equipment and operation technologies are required and the food processing and storage are also simple with small investment, so the food production and supply cost in the space can be minimized.

What is claimed is:

1. A method for achieving a mini space farm and food regeneration for a long term space living environment for humans, the environment is comprised of bio-wastes and organic plastics, within the environment six types of recycling animals are fed the bio-wastes and organic plastics;

these six recycling animals used in the method for achieving a mini space farm and food regeneration environment are as follows:
1. Housefly Larvae—Maggot;
2. Mealworm;
3. Superworm;
4. *Tubifex;*
5. Cladoceran;
6. Earthworm;

by using the following process combined with the six recycling animals, a mini space farm and food regeneration environment will be achieved, comprising:

using the biomass of the six recycling animals, combined with inedible plants parts as the feedstuff for feeding edible animals comprising poultry, aquatics animals, amphibians and livestock; and using the residues of rearing the recycling animals as the fertilizer for cultivating plants of crops, vegetables, mushroom, edible algae of *Nostoc sphaeroides* kutzing, and germ; and using the edible animals and plants as nourishing food for the humans in the space.

2. The method defined in claim 1, further comprising: reproducing the recycling animals and edible animals in space by freezing their eggs and oosperms in liquid nitrogen for long-term storage and thawing them any time in order to recover their ability to reproduce and achieve normal growth in the space.

3. The method defined in claim 1, further comprising:
rearing these recycling animals, edible animals, and plants in the same cabin by piling up breeding boxes, cages, trays and tanks on a shelf that has high density, minimum volume and weight for achieving the mini farm in the space.

4. The method defined in claim 1, further comprising:
rearing aquatic edible animals and aquatic plants as a food production ecosystem in circulating water tank series; feeding the recycling animals and inedible plants to the aquatic edible animals as feed; recycling the wastes of the aquatic edible animals by aquatic recycling animals and bacteria; and the aquatic plants consist of some algae and plants, mainly *Nostoc sphaeroides* kutzing which fed with $CO_2$ and $N_2$, and produce high nutrition biomass as human food and also $O_2$ for aquatic animal's needs.

5. The method defined in claim 1, further comprising:
raising animals by feeding the edible animals the maggots, mealworm and superworm, and their pupa while alive; also by feeding the edible animals the powder of maggot, mealworm and superworm;

using the edible animals and its egg, and the maggot powder as healthy food for humans which in turn assists in resisting radiation and improving immune abilities;

using the edible animals and its egg, and the powder of mealworm and Superworm as healthy food for humans which may reduce the level of the blood lipids and cholesterol, this in turn may improve human's cardiac vascular function and cure hyperlipidemia.

* * * * *